United States Patent [19]
Chedid et al.

[11] 4,094,971
[45] June 13, 1978

[54] IMMUNOLOGICAL ADJUVANT AGENTS ACTIVE IN AQUEOUS SOLUTION

[75] Inventors: Louis A. Chedid, Paris; Françoise Marguerite Audibert, Neuilly-sur-Seine, both of France

[73] Assignee: Agence Nationale de Valorisation de la Recherche, Neuilly-sur-Seine, France

[21] Appl. No.: 717,509

[22] Filed: Aug. 25, 1976

[30] Foreign Application Priority Data
Aug. 29, 1975 France .................. 75 26704

[51] Int. Cl.$^2$ ............................................. A61K 39/02
[52] U.S. Cl. ........................................ 424/92; 424/88; 424/177; 260/112.5 R
[58] Field of Search ................ 195/29, 96; 260/112.5; 424/177, 88, 92; 536/18

[56] References Cited
U.S. PATENT DOCUMENTS

| | | | |
|---|---|---|---|
| 3,956,481 | 5/1976 | Jolles et al. | 424/92 |
| 4,013,788 | 3/1977 | Jolles et al. | 424/92 |
| 4,014,992 | 3/1977 | Jolles et al. | 424/92 |
| 4,036,953 | 7/1977 | Adam et al. | 424/92 |
| 4,042,678 | 8/1977 | Ciorbaru et al. | 424/92 X |

*Primary Examiner*—Lionel M. Shapiro
*Attorney, Agent, or Firm*—Weiser, Stapler & Spivak

[57] ABSTRACT

Immunological adjuvants obtainable from already-known water-soluble adjuvants containing peptidoglycane fragments, which include saccharide units formed from N-acetylglucosamine and from an N-acylmuramic acid wherein the acyl group is a glycolyl or acetyl group and to the muramyl group there are attached peptide chains, by modification of said already-known water-soluble adjuvants so that they bear acylating groups derived from physiologically-acceptable carboxylic polyacids, especially carboxylic diacids, and wherein preferably the acylating groups themselves include free carboxylic acid groups, for instance being derived from phthalic acid or succinic acid.

40 Claims, No Drawings

IMMUNOLOGICAL ADJUVANT AGENTS ACTIVE IN AQUEOUS SOLUTION

This invention is concerned with agents effective as immunological adjuvants to stimulate immune reactions, in a host, to antigens of different kinds. The invention relates in particular to adjuvant agents which serve to reinforce and to enhance the action of weak immunogens.

The invention more especially relates to agents effective as adjuvants capable of use for the immunisation of man and of warm-blooded animals against bacterial, viral and parasitic infections, and against different tissue antigens of either normal or pathological origin, notably against tumours.

Various compositions or substances possessing adjuvant properties have been described.

A first family of compositions or substances known as having adjuvant properties is constituted by the lipopolysaccharides extracted from Gram-negative bacteria. Unfortunately these products, although very active, also display an extremely high toxicity which renders any possibility of using them in therapeutic treatments exceedingly difficult if not impossible. It has already been proposed chemically to modify these lipopolysaccharides in order to reduce their toxicity, in particular by recourse to acylation reactions upon these lipopolysaccharides with acid, such as succinic acid. It has however been found that this succinylation results in a certain loss of the adjuvant activity of the product obtained, as compared with that of the starting lipopolysaccharide — notably when the adjuvant character of the products under investigation is evaluated in terms of their ability to promote the production by the host of antibodies with respect to the antigens administered with this product — even if the reduction observed in the toxicity of these products is still more significant.

The grave inconvenience caused by the toxicity is eliminated when recourse is had to water-soluble adjuvant agents based upon peptidoglycane [break-down] fragments which can be obtained starting from the cellular walls of procaryotes bacteria. These adjuvant agents can possibly include other groups, for example can contain an arabinogalactane group when they have been obtained starting from mycobacteria or from Nocardia. Preferred adjuvant agents are those described in French Patent Applications and Certificates of Addition No. 71-41610 dated Nov. 19, 1971, on which is based U.S. patent application Ser. No. 307,614 filed Nov. 17, 1972, from which issued U.S. Pat. No. 4,036,953 on July 17, 1977 No. 72-22120 dated 19th June 1972 and No. 73-37806 dated Oct. 23, 1973 (two patents of addition of the earlier 1971 patent) and on which application is based pending U.S. patent application Ser. No 516,991 filed Oct. 22, 1974.

These adjuvant agents are extremely interesting in as much as they are simultaneously both water-soluble and more or less without toxicity. Although in certain experimental tests they have shown themselves to possess a certain adjuvant activity when administered in conjunction with an antigen in an isotonic solution of sodium chloride, this activity does not display itself to a significant extent when the adjuvant agent and the antigen are administered in a water-oil emulsion. This mode of administration moreover presents some difficulties, to the extent that the oils generally employed to make up these emulsions are not capable of metabolisation. Such for example is the case with the oil employed to make up the incomplete adjuvant of Freund (FIA).

It is the object of this invention to modify these water-soluble and substantially non-toxic adjuvant agents, based upon compounds containing peptidoglycane [break-down] fragments extracted from procaryotes bacteria, so that they fulfil practical requirements better than at present, notably in that they shall be able to manifest an adjuvant activity when administered in conjunction with an antigen in an isotonic aqueous solution, in the absence of oil, this activity preferably being substantially equal, if not superior, to that displayed by the same adjuvant agents, before their modification in accordance with this invention in a water-oil emulsion.

It is also an object of this invention to provide a process for the manufacture of such modified adjuvant agents, based upon peptidoglycane [break-down] fragments.

The adjuvant agents according to the invention, which are derived from water-soluble adjuvants containing peptidoglycane [break-down] fragments, are characterized in that they bear acylated groups derived from physiologically-acceptable carboxylic polyacids, these acylation groups themselves if desired bearing free carboxylic groups. Preferred acylation groups are those which are derived from phthalic anhydride or from succinic anhydride. It goes without saying that these acylation groups can be derived from any analogous polycarboxylic acid [which is] physiologically-acceptable and capable of inducing an increase in the adjuvant activity of known adjuvant agents based upon peptidoglycane [break-down] fragments, when these are administered with the antigen in an isotonic aqueous solution.

The process according to the invention for improving the activity of water-soluble adjuvant agents based upon peptido-glycane [break-down] fragments, when administered with an antigen in a saline solution is characterized in that these agents are subjected to an acylation reaction with a physiologically-acceptable carboxylic acid, this acid being preferably employed in the form of its anhydride.

Generally speaking, the invention is applicable to water-soluble adjuvant agents which in their molecules contain saccharide units formed from N-acetylglucosamine and of N-acyl-muramic acid, in the formula of which the acyl group is specifically of the glycolyl or acetyl type, these agents also containing a peptide chain attached to the muramyl group.

Preferred water-soluble adjuvant agents employed in the operation of the process according to the invention are those which have been described in the Patent Applications and Certificates of Addition already identified above and obtained by the processes which have there been described or analogous adjuvants.

The chemical analysis of the majority of the adjuvants obtained by the processes described in the Patent Application No. 71-41610 and in the Certificate of Addition No. 72-22120 reveals that they additionally contain some neutral sugars, notably some galactose and some arabinose. It should be noted that these adjuvant agents can be obtained starting from micro-organisms such as the mycobacteria or Nocardia. According to a preferred method (first Addition No. 72-22120) these micro-organisms are cultivated, harvested and then successively freed from the free lipids and from the waxes, from the proteins and from the nucleic acids which they contain, for example respectively by means of solvents, proteolytic enzymes and of desoxy-ribonuclease, the solid product thus obtained being finally treated by a murolytic enzyme or by a muramidase such as lysozyme in an aqueous solution. The resultant aqueous phase which contains the adjuvant agent is filtered, possibly purified advantageously by filtration through a molecular sieve, and the adjuvant is possibly isolated by lyophilisation. This method of preparation is not the only one possible to obtain these adjuvant agents. Alternatively one can specifically operate by following the procedure described in Pat. No. 71–41,610. According to this Patent the same micro-organisms are subjected to a preliminary treatment aimed at separating and recovering the cellular walls, the rest of the treatment applied to the initially-separated cellular walls containing the successive stages indicated above.

A carboxylic polyacid, or an anhydride or a chloride of the carboxylic polyacid is advantageously used to carry out the acylation. In a particularly preferred manner of proceeding, there is employed phthalic anhydride, succinic anhydride or an analogous anhydride capable of acylating the initial adjuvant agents and also of introducing carboxylic groups into the compound resulting from the acylation.

The reaction is advantageously carried out in solution in a basic anhydrous medium, preferably made up from solvents such as formamide, pyridine or analogous solvents in which the initial adjuvant agents are soluble, or alternatively in a mixture of several of these. The preferred solvents are those which, upon contact with water, give a basic reaction, characterised by a pH lying between 7 and about 10.

The reaction is carried out at a temperature which normally will not exceed 50° C, and preferably at ambient temperature.

The acylation reaction is relatively slow. In order to secure a sufficient acylation of the initial adjuvant agents, the length of reaction is not usually less than 6 hours. If necessary the reaction is continued, possibly by repeating the operation upon the product emerging from a first acylation, in order with advantage to be able to push the latter further. Moreover in order to facilitate the reaction and to increase the acylation yield, it is advantageous to operate with an excess of the acylating agent.

The acylation equally can be effected with the acids corresponding to the aforesaid anhydrides, in a medium which then can contain water. It is however clear that in such a case the acylation reactions will be still slower than when one is using anhydrides in an anhydrous medium.

After the acylation, the product of the reaction which is soluble in the reaction medium can be recovered, after separation from the solvents and from any reagents which have not reacted: for example, when the solvents employed are miscible with water, the reaction medium can be diluted with water and thereafter one carries out one or more dialyses against distilled water, which makes it possible to eliminate the solvents and the excess of the acylating agent. It goes without saying that any other method of separation can be employed. It is possible to have recourse to filtration through molecular sieves, for example through reticulated dextrane gels of the kind known under the Trade Name SEPHADEX.

The acylated adjuvants thus obtained can be lyophilised. They can — for example before their use — be neutralised if necessary with the aid of a solution of a physiologically-acceptable metal salt, for example sodium bicarbonate, the salts finally obtained being in their turn lyophilised.

The invention thus equally relates to the salts of the acylated adjuvants, no matter whether the metallic salts or salts involving physiologically-acceptable organic bases.

It is remarkable that the acylation of the water-soluble adjuvant agents of the type indicated hereinabove results in an increase, which can be extremely significant, in their adjuvant activity, when they are administered in aqueous solutions.

It goes without saying that it is worthwhile to introduce into the initial adjuvants a proportion of acylating groups sufficient to ensure that the adjuvant activity in an aqueous solution shall be greatly increased as compared with that which could initially be observed for certain of the adjuvants, before their modification.

When the acylating agent is phthalic anhydride, acylated products can be obtained containing up to 70% by weight of phthalyl grouping measured in terms of the total weight of the phthalyl derivative obtained.

A modified adjuvant agent is obtained having a significant adjuvant activity in aqueous solution, when the weight ratio of the phthalyl groupings in this modified adjuvant agent is of the order of 67%, the weight ratio of the adjuvant initially employed then being of the order of 33%.

When the acylating agent is succinic anhydride, there is easily obtained a succinylated derivative containing up to 50% by weight of succinylated groups. Likewise succinylated adjuvants containing 50% by weight of succinylating groups and 50% by weight of the adjuvant initially employed display an increased adjuvant activity in aqueous solutions.

Without in any way suggesting that the ranges indicated below should be ragarded regarded limiting, it can be emphasised that phthalylated products containing from 30% to 50% by weight of the initial adjuvant agent and succinylated adjuvants containing from 50% to 70% by weight of the adjuvant initially employed display a strong adjuvant activity in aqueous solution.

In general it can be observed that the modified adjuvant agents according to the invention possess a structure which derives from that of the adjuvants from which they come, by replacement of the hydroxyl functions originally borne by the latter by means of acylated chains derived frm the acylating agent employed. Without being bound by any theoretical considerations, it is possible to formulate a hypothesis that it is the hydroxyl groups carried by the sugars or amino-sugars contained in the adjuvants initially employed which undergo the said acylation.

The acylated adjuvant agents according to the invention are stable at a temperature of 4° C over a period of at least several months, and can be lyophilised without loss of activity. They are soluble in water. Their solutions studied by analytical ultra-centrifuging behave themselves like a slightly-dispersed homogeneous macromolecular system comparable to that of the non-acylated initial adjuvant from which they derive.

The acylated adjuvant agents which are the subject of this invention, as described hereinabove, display a strong adjuvant activity when they are administered in the aqueous phase, unlike the non-acylated adjuvants from which they come, which are not sufficiently efficacious whey they are administered in a water-oil emulsion.

It is a further object of the invention to provide immunising compositions which specifically contain an effective dose of at least one acylated adjuvant according to the invention, possibly first salified.

Such a composition will advantageously take the form of a physiologically tolerable aqueous solution, either capable of injection or suitable for use in making up injectable solutions.

Other details of the invention will appear in the course of the following example describing the preparation of acylated adjuvant agents, and tests to determine the pharmacological properties of these agents.

I - EXAMPLE

Preparation of acylated adjuvant agents

The initial adjuvant agent (WSA) was obtained starting from whole cells of *M. smeqmatis* (ATCC NBR 21 732) according to the procedure described in the Addition No. 72-22120.

This preparation was as follows.

The bacteria were cultivated on Sauton medium. They were harvested by filtration, and washed several times with distilled water. They were then placed in the cartridge (thimble) of a Soxhlet extractor and extracted successively at reflux with acetone, with ethyl alcohol, with chloroform and with a chloroform-methanol (87 : 13) mixture, then dried with ether. They are next washed by putting into suspension in one hundred times their weight of water, then centrifuged. This washing is repeated twice more with water, then twice with 0.1 M ammonium acetate at pH 6.2. The product obtained is finally put back into suspension in a weight of buffer equal to one hundred times the initial weight of the bacteria; lysozyme is added to their suspension(1% by weight of the delipidised bacteria). After incubation for 18 hours at 37° C in the presence of several drops of toluene, with the intention of avoiding contamination of the bacteria the suspension is filtered. The preparation is put back into suspension in ammonium acetate and re-incubated in the presence of lysozyme under the same conditions as for the first incubation. The filtrates corresponding to the two incubations are combined and lyophilised.

The phthalylated and succinylated derivatives of WSA are prepared as follows: 100 mg of WSA are treated with 1 g of phthalic anhydride or of succinic anhydride in solution in a mixture 5 ml of formamide and of 5 ml of pyridine wholly freed from moisture. The reaction medium is maintained at ambient temperature with agitation for 24 hours.

The reaction mixture is put into solution in 40 ml of distilled water. The solution thus formed is then dialysed against distilled water for 48 hours. The solution containing the acylated derivative is neutralised by a solution of sodium bicarbonate, then dialysed against distilled water. The solution is finally concentrated and lyophilised.

The weight ratio of the initial adjuvant agent (WSA) retained in the acylated product, prepared as has just been described, is of the order of 50% by weight for the succinylated derivative and of the order of 33% by weight for the phthalylated derivative, measured in terms of the total weight of the acylated product.

The analysis of the phthalylated and succinylated products and of the initial WSA by ultra-centrifuging shows moreover the absence of polydispersion; the product obtained is thus homogeneous molar mass. The increment in the sedimentation factor, $S = 3.75$ for the phthalylated derivative as against $S = 1.89$ for the initial WSA, also reflects the increase in the molecular mass resulting from the attachment of the phthalyl groups.

The ultra-centrifuging steps were carried out in saline solutions buffered at pH 7 by means of borate. The concentration of the product under study was 1%. The experiment was carried out at 20° C and at 59,780 revolutions/minute, in an ultra-centrifuge of the SPINCO brand, Model E.

II - Pharmacological Properties of the Acylated Adjuvant Agents Obtained

1. Determination of the toxicity of the acylated derivatives

In this test, the 50% -lethal dose ($LD_{50}$) of the phthalylated derivative obtained from the example was compared with those of respectively the initial adjuvant (WSA) from which it was derived and of the lipopolysaccharide (LPS) extracted from the cells of *S. enteriditis*, by the method of extraction with water-phenol mixture: it must be recalled that LPS, although it displays adjuvant properties, is not capable of being used as such, because of its very high toxicity.

The method employed in this determination was that described by L. Chedid et al, in Ann. N.Y. Acd. Sci., (1966) 133, 712.

The determination was carried out on two-month-old Swiss mice. The products studied were administered by intravenous injection. In this way it has been established that the 50% -lethal dose for LPS in normal mice is of the order of 300 micrograms (300 μg). It is no more than 0.02 μg when the mice have first been subjected to a surrenalectomy. Under the same conditions, the mice subjected to surrenalectomy into which either WSA or the corresponding phthalylated derivative (SPWSA) have been injected all survived at an injection of 300 μg.

This shows that on the one hand the acylated adjuvants according to the invention are practically speaking non-toxic at doses (300 μg) at which, as will be shown from what follows, they possess a good efficacy as adjuvants, and on the other hand it shows also that they are in this particular respect comparable to the WSA from which they have been derived.

2. Modification of the antigenicity

The determination of the antigen-antibody reactions is carried out according to the double diffusion method of Ouchterlony.

According to this method adjacent cavities or "pits" (or wells) are formed in an agar-based medium (of the kind marketed by DIFCO and buffered with a 0.025 M borate with 0.08 M of NaCl) and into these separate wells there are introduced 50 microgram doses of the respectively WSA and of phthalylated WSA, and in quite separate and distinct wells, close to the first-mentioned ones, there are also introduced respectively WSA antiserum and phthalylated-WSA antiserum.

The appearance is then observed of bands of precipitation between the serum wells and the corresponding antigen wells. On the other hand no cross-reaction is detectable. The antigenicity of the phthalylated derivative is thus quite specific. It may be noted that the antisera employed were prepared beforehand in the following manner:

Doses of 1 mg of the compound under study in 1 ml of an oil-in-water emulsion were injected into rabbits. Each rabbit received 4 injections per week over a period of 1 month, with a repeat two weeks after the last injection. The blood is finally recovered 6 days after the repeat.

3. Inducement of Arthritis in Mice

Quite apart from the investigation of toxicity, the complete innocuousness of the compounds according to the invention has been demonstrated in comparison to their effectiveness and to that of other adjuvants, notably those containing cells of myco-bacteria (of the Freund complete adjuvant type) by the inducement of arthritis test.

An adjuvant arthritis was developed in mice by injection of various mycobacterial preparations into the plantar pad of the rear paws. The experimental arthritis thus induced manifests itself at the site of the paw in which the injection was made in particular by an increment of volume and consequently in weight. This change reaches a maximum after about 2 weeks. Measurements are taken 21 days after the injection, by measuring the weight of paws severed at the level of the ankle. The respective weights of the right and left paws are compared, only one of which has received the injection, the other serving as a basis for comparison. The substances under investigation were injected with Freund incomplete adjuvant (FIA). Some control mice received only FIA. The results reported in Table 1 below show that the injection of cells of *M. smegmatis* results in a great increase in the weight of the paw. On the other hand the injection of WSA or of SP WSA in FIA does not produce any greater effect than that injection of FIA alone.

Thus no detectable articular inflammatory reaction is observed following upon the injection of the product according to the invention.

Table 1

| Treatment | Weight of the Paw left | right | Percentage increase in weight |
| --- | --- | --- | --- |
| FIA control | 188 | 244 | 30 |
| FIA + cells of M. Smegmatis 25 μg | 174 | 615 | 261 |
| FIA + WSA 250 μg | 189 | 261 | 37 |
| FIA + SP 250 μg | 187 | 254 | 36 |

4. Absence of the delayed hypersensitivity reaction of the tuberculin type in rabbit sensitised by Freund's complete adjuvant (FCA)

Some Hartley rabbits were sensitised by injection into their rear paws either of Freund's complete adjuvant (FCA) or of Freund's incomplete adjuvant (FIA) containing some WSA prepared as described in the example above. Some control animals received only FIA.

18 days after the sensitisation 0.1 ml of a saline solution was injected which contained 10 μg either of WSA or of the phthalylated WSA (SP WSA).

48 hours after this injection the diameter of the hardened tissue around the site of injection was noted. The results set out in Table 2 below are expressed in millimeters.

A hypersensitivity reaction of the tuberculin type to the injection of WSA was observed no matter whether the sensitisation had been created with FCA or with FIA to which WSA had been added; on the other hand there was a total absence of reaction to SP WSA in every case, just as with the controls. These results, taken in conjunction with those already noted under 2., demonstrate the absence of any crossed activity between WSA and its acylated derivative, and the appearance in the latter of a new antigenic structure distinct from that present in the mycobacteria.

Table 2.

| Treatment | Skin Test WSA 10 μg | SP WSA 10 μg |
| --- | --- | --- |
| FIA (controls) | 0,0,0,0,0,0, | 0,0,0,0,0,0, |
| FCA | 4,9,7,0,9,8 | 0,0,0,0,0,0, |
| FIA + WSA 50 μg | 11,13,7,9,13,8 | 0,0,0,0,0,0. |

5. Demonstration of the adjuvant properties of the compounds according to the invention, when injected in isotonic saline solution.

In the following tests the adjuvant activity of the compounds according to the invention has been studied. This activity was measured by the responses obtained, after injection of adjuvants, with the antigens constituted by the albumin of bovine serum (BSA) or by influenza virus.

A. Response to BSA

The tests were carried out on mice which received 0.5 mg of BSA with different doses of various adjuvants, the whole in isotonic saline solution. The immune reaction is enhanced by a repeat constituted by a fresh dose of BSA in the isotonic solution but without adjuvant. The repeat was effected 30 days after the first injection.

The dosage of antibodies for these different tests was made up at the time by a passive hemagglutination method and by the so-called capacity of fixation of the antigen by the serum method, a measurement made by means of BSA labelled with iodine 125. These methods have been described in various publications, amongst them in particular for the passive hemagglutination the article by A. A. Hirata and M. W. Brandiss in J. Immunol., (1968), 100, 641–648, and as regards the fixation of the antigen the work of P. Minden and S. Farr, as described on page 463 of the *Handbook of Experimental Immunology*, edited by D. M. Weir, published by Blackwell Scientific Publications, Oxford and Edinburgh, 1967.

(a) In a first series of tests, various doses of WSA and of LPS were administered with the isotonic saline solution of BSA. The results of these tests, set out in Table 3 below, show that by comparison with control animals which received only BSA the increase in the antibody count is significant with LPS principally in the framework of the secondary immune reaction (after the repeat carried out 30 days after the first injection). On the contrary, no significant increase was obtained with WSA. The figures correspond to the averages of the antibody titres, expressed either by the greatest dilution of serum which gave an agglutination or by the dilution of serum capable of precipitating 33% of the added radio-active antigen at constant dosage.

Table 3.

| Treatment | Primary Response 14th day | | 28th day | | Secondary Response 34th day | | 36th day | |
| --- | --- | --- | --- | --- | --- | --- | --- | --- |
| | PHA | ABC | PHA | ABC | PHA | ABC | PHA | ABC |
| Controls | <12 | <20 | <12 | <20 | <12 | <20 | 6 | 45 |
| LPS 30 μg | <12 | <20 | 6.2 | <20 | 100 | 120 | 700 | 500 |
| LPS 100 μg | <12 | <20 | 6 | <20 | 50 | 110 | 1300 | 1600 |

Table 3.-continued

| | Primary Response | | | | Secondary Response | | | |
|---|---|---|---|---|---|---|---|---|
| | 14th day | | 28th day | | 34th day | | 36th day | |
| Treatment | PHA | ABC | PHA | ABC | PHA | ABC | PHA | ABC |
| WSA 30 μg | <12 | <20 | <12 | <20 | <12 | <20 | <12 | <20 |
| WSA 100 μg | <12 | <20 | <12 | <20 | <12 | <20 | 3 | <20 |
| WSA 300 μg | <12 | <20 | <12 | <20 | <12 | <20 | <12 | <20 |

PHA = Passive Hemagglutination
ABC = Antigen Binding Capacity.

(b) In a second series of tests similar to those described above the adjuvant activities of WSA and of its "phthalylated" derivatives (SP WSA) and of its "succinylated" derivatives (SU WSA) prepared as described in the above Example was compared. The WSA was employed at dosage levels of 300 μg. As regards the acylated compounds, the indicated dosages are related to those of the WSA contained in the product under consideration; it is moreover the same for the dosages appearing in Tables which follow.

The results of these tests are set out in Table 4 and as with the previous test they demonstrate the inactivity of WSA in saline solution. The mice treated with BSA and with one of the "acylated" derivatives of WSA display on the contrary a sharply increased antibody count which in the case of the phthalylated derivative manifests itself even in the course of the primary reaction. This reaction is as a first approximation comparable to that obtained in the previous test with LPS.

Table 4.

| | Primary Reaction | | | | Secondary Reaction | | | |
|---|---|---|---|---|---|---|---|---|
| | 14th day | | 28th day | | 34th day | | 36th day | |
| Treatment | PHA | ABC | PHA | ABC | PHA | ABC | PHA | ABC |
| Controls | <3 | <20 | <3 | <20 | 3 | <20 | 4 | <20 |
| WSA 300 μg | <3 | <20 | <3 | <20 | 6 | <20 | 6 | 65 |
| SU WSA 300 μg | <3 | <20 | 3 | <20 | 100 | 110 | 1600 | 400 |
| SP WSA 300 μg | 25 | 70 | 50 | 110 | 400 | 400 | 1700 | 400 |

(c) A third series of tests was carried out in order directly to compare the activities of different dosages of LPS and of the succinylated and phthalylated derivatives of WSA. The conditions for these tests were the same as previously. The results given in Table 5 below show that the adjuvant activity of a dose of 300 μg of the derivatives of WSA is practically equivalent to that of 100 μg of LPS. The derivatives according to the invention on the other hand do not show any toxicity at these dosages, as has been shown in the Example.

Table 5.

| | Primary Reaction | | | | Secondary Reaction | | | |
|---|---|---|---|---|---|---|---|---|
| | 14th day | | 28th day | | 34th day | | 36th day | |
| Treatment | PHA | ABC | PHA | ABC | PHA | ABC | PHA | ABC |
| Control | 3 | 20 | 3 | 20 | 3 | 20 | 10 | 30 |
| LPS 30 μg | 3 | 20 | 6 | 20 | 100 | 120 | 715 | 530 |
| LPS 100 μg | 3 | 20 | 3 | 20 | 400 | 320 | 1550 | 2000 |
| SU WSA 100 μg | 3 | 20 | 3 | 20 | 25 | 65 | 330 | 240 |
| SU WSA 300 μg | 3 | 20 | 6.2 | 20 | 200 | 240 | 1300 | 600 |
| SP WSA 300 μg | 3 | 20 | 25 | 75 | 400 | 400 | 1550 | 620 |

B. Reaction to influenza virus

The adjuvant activity of the products according to the invention has similarly been tested against influenza vaccine. The dose of vaccine injected was 50 units. The injection was intraperitoneal; the test animals also received some SP WSA at the dosages indicated in Table 6; the control animals received only the vaccine; a repeat with the vaccine, without adjuvant, was carried out 30 days later in all the animals. The level of antibodies formed was estimated by inhibition of the hemagglutination of chicken erythrocytes according to the method suggested by the World Health Organisation Committee (1953).

The results given in Table 6 show the very marked influence of the adjuvant and of the dosage thereof upon the increase in the formation of antibodies, in particular in the secondary reaction. The count of antibodies formed was approximately double at 30 μg of SP WSA, and was about quintupled at a dose of 100 μg.

Table 6.

| | Primary Reaction | Secondary Reaction | |
|---|---|---|---|
| Treatment | 21st day | 34th day | 36th day |
| Controls | not detectable | 15 | 100 |
| SP WSA 30 μg | not detectable | 55 | 205 |
| SP WSA 100 μg | 30 | 100 | 515 |

Thus the adjuvants obtained according to the invention possess a considerable activity, are free from toxicity and unpleasant secondary effects and display their excellent properties when they are administered in aqueous solution.

Thus one has at one's disposal adjuvant substances which can be employed to increase the effectiveness of vaccines of bacterial or viral origin more especially if they are weak immunogens. They can in particular be employed to promote the immunisation of the host (whether human or animal patients) against infections of bacterial or viral origin, antigens of tumors, protozoan antigens, etc. They are equally effective for the manufacture of serums containing antibodies active against these antigens. These modified adjuvant agents can be administered with the antigen, the vaccine or the aforesaid antibodies in aqueous solutions.

The administration of the modified adjuvants according to the invention can be achieved in the form of aqueous compositions and in the form of sterile, injectable, aqueous solutions, by intramuscular, intradermal or subcutaneous injection, or by scarification (vaccination).

It goes without saying, and as indeed appears anyway from what has already been said previously, the invention is in no way limited to those of its modes of application and modes of achievement which have been particularly described; it extends on the contrary to all possible variations thereof.

We claim:

1. A compound, a water-soluble adjuvant which has immunological activity in-vivo when administered to a host in an oil-free aqueous solution, which adjuvant is an acylated peptidoglycane fragment having saccharide units of N-acetylglucosamine and N-acylmuramyl, the acyl radical being glycolyl or acetyl, and the muramyl group having peptide chains linked thereto,
    wherein the acyl groups of the peptidoglycane are of a physiologically acceptable polycarboxylic acid, or its anhydride, and the physiologically acceptable salts of the acylated compound.

2. The immunological adjuvant according to claim 1, wherein the carboxylic polyacids are carboxylic diacids.

3. The immunological adjuvant according to claim 1 wherein the acyl group is a glycolyl.

4. The immunological adjuvant according to claim 1, wherein the acylating groups themselves include free carboxylic acid groups.

5. The immunological adjuvant according to claim 3, wherein the acylating groups themselves include free carboxylic acid groups.

6. The immunological adjuvant according to claim 1, wherein the acylating groups are derived from phthalic acid or its anhydride.

7. The immunological adjuvant according to claim 6, wherein the phthalyl groups are present in the modified adjuvant in a weight ratio lying within the range of from 50% to about 70% of the total weight of the modified adjuvant.

8. The immunological adjuvant according to claim 7, wherein the phthalyl groups are present in a weight ratio of the order of 67%.

9. The immunological adjuvant according to claim 1, wherein the acylating groups are derived from succinic acid.

10. The immunological adjuvant according to claim 9, wherein the succinyl groups are present in the modified adjuvant in a weight ratio lying within the range of from 30% to about 50% of the total weight of the modified adjuvant.

11. The immunological adjuvant according to claim 10, wherein the succinyl groups are present in a weight ratio of the order of 50%.

12. An immunological adjuvant composition comprising the immunological adjuvant according to claim 1 and a pharmacologically-acceptable solvent vehicle free from oil.

13. The immunological adjuvant composition according to claim 12 wherein the vehicle is an isotonic, sterile and injectable medium.

14. The immunological adjuvant composition according to claim 12 which comprises also a vaccinating antigen.

15. Process for preparing immunological adjuvants according to claim 1, wherein the acylating agent is selected from the group consisting of a physiologically-acceptable polycarboxylic acic and its anhydride.

16. The process according to claim 15 wherein the polycarboxylic acid or anhydride employed cause the introduction into said adjuvants of acylating groups containing free carboxylic acid groups.

17. The process according to claim 15, wherein the diacid used in selected from the group consisting of phthalic acid, phthalic anhydride, succinic acid and succinic anhydride.

18. The process according to claim 15, wherein the acylation is affected with the anhydride in an anhydrous basic solvent in which the immunological adjuvant containing peptidoglycane fragment used as starting material is soluble.

19. The process according to claim 18, wherein the basic solvent employed is one which when in contact with water will give a basic pH between 7 and about 10.

20. The process according to claim 18, wherein the acylation is carried out at a temperature at most equal to 50° C.

21. The process according to claim 18, wherein the solvent used is formamide.

22. The process according to claim 18, wherein the solvent used is pyridine.

23. The process according to claim 18, wherein one operates with an excess of the acylating agent.

24. The immunological adjuvant of claim 1 wherein the acyl group is acetyl.

25. The adjuvant of claim 1 wherein the peptidoglycan fragments contain neutral sugars selected from the group consisting of galactone and arabinose.

26. The adjuvant of claim 1 wherein the acyl group is phthalyl or succinyl.

27. The immunological adjuvant of claim 1 which is antigenically distinct from the corresponding unacylated compound.

28. The immunological adjuvant composition of claim 12 wherein the adjuvant is antigenically distinct from the corresponding unacylated compound.

29. The immunological adjuvant of claim 1 immunologically effective against an antigen and a serum containing antibodies effective against the antigen.

30. The method of promoting the immunization of a host which comprises administering to the host, a therapeutically effective amount of the composition of claim 12.

31. The method of claim 30 wherein the adjuvant composition is administered in an isotonic, sterile, injectable medium.

32. The method of claim 30 wherein the vaccine is administered in an isotonic, sterile, injectable medium.

33. The method of claim 30 wherein the serum is administered in an isotonic, sterile, injectable medium.

34. An immunological adjuvant which is a water-soluble compound which is a saccharide having N-acetylglucosamine group and an N-acetyl muramic acid group, wherein the acyl is glycolyl or acetyl and having a peptide chain linked to the muramyl radical, which compound is acylated, the cylating radical being selected from the group consisting of phthalyl or succinyl thereof, in an isotonic, sterile, injectable aqueous medium.

35. The metallic salt of the compounds of claim 34.

36. The salt of the compounds of claim 34 and an organic base.

37. A modified, water-soluble immunological adjuvant which is formed of break down fragments of cell-wall peptidoglycans containing saccharide units formed from N-acetyl glucosaminyl and N-acetylmuramyl groups, wherein the acyl groups is glycolyl or acetyl, and a peptide is linked to the muramyl group, which water-soluble immunological adjuvant carries modification-acylation groups fixed thereon and derived from physiologically-acceptable polycarboxylic acids of the type and in a proportion such as to enable said peptidoglycane break-down fragments to exert their adjuvant immunological activity in vivo when administered in the form of an oil-free, aqueous saline solution.

38. The modified, water-soluble immunological adjuvant according to claim 37 wherein said peptidoglycan fragments also contain neutral sugar groups other than amino-sugars.

39. The modified, water-soluble immunological adjuvant according to claim 38 wherein said neutral sugar form arabino-galactane groups.

40. A modified, water-soluble immunological adjuvant according to claim 37 which is antigenically distinct from the non-modified water-soluble immunological adjuvant.

* * * * *